United States Patent
Laredo et al.

(10) Patent No.: US 8,449,610 B2
(45) Date of Patent: May 28, 2013

(54) HIGH REFRACTIVE INDEX, ACRYLIC OPHTHALMIC DEVICE MATERIALS WITH REDUCED GLISTENINGS

(75) Inventors: Walter R. Laredo, Fort Worth, TX (US); Charles Freeman, Granbury, TX (US); Thomas A. Callaghan, Fort Worth, TX (US)

(73) Assignee: Novartis AG, Basel (CH)

( * ) Notice: Subject to any disclaimer, the term of this patent is extended or adjusted under 35 U.S.C. 154(b) by 158 days.

(21) Appl. No.: 13/164,290

(22) Filed: Jun. 20, 2011

(65) Prior Publication Data

US 2011/0313518 A1 Dec. 22, 2011

Related U.S. Application Data

(60) Provisional application No. 61/356,963, filed on Jun. 21, 2010.

(51) Int. Cl.
| | | |
|---|---|---|
| *A61F 2/16* | (2006.01) | |
| *G02B 1/04* | (2006.01) | |
| *C08F 265/04* | (2006.01) | |
| *C08G 77/04* | (2006.01) | |
| *C08L 71/02* | (2006.01) | |

(52) U.S. Cl.
CPC ............... *A61F 2/1602* (2013.01); *C08L 71/02* (2013.01)
USPC .......... 623/6.31; 523/106; 523/107; 525/303; 525/304; 528/16

(58) Field of Classification Search
CPC .................................................... A61F 2/1602
USPC ................ 623/6.31; 523/106, 107; 525/303, 525/304
See application file for complete search history.

(56) References Cited

U.S. PATENT DOCUMENTS

| | | | |
|---|---|---|---|
| 4,304,895 | A | 12/1981 | Loshaek |
| 4,528,311 | A | 7/1985 | Beard et al. |
| 5,290,892 | A | 3/1994 | Namdaran et al. |
| 5,331,073 | A | 7/1994 | Weinschenk et al. |
| 5,470,932 | A | 11/1995 | Jinkerson |
| 5,693,095 | A | 12/1997 | Freeman et al. |
| 6,353,069 | B1 | 3/2002 | Freeman et al. |
| 6,528,602 | B1 | 3/2003 | Freeman et al. |
| 6,653,422 | B2 | 11/2003 | Freeman et al. |
| 7,585,900 | B2 | 9/2009 | Cordova et al. |
| 7,714,039 | B2 | 5/2010 | Cordova et al. |
| 7,790,824 | B2 | 9/2010 | Freeman |
| 7,790,825 | B2 | 9/2010 | Lehman et al. |
| 7,799,845 | B2 | 9/2010 | Schlueter |
| 7,888,403 | B2 | 2/2011 | Schlueter |
| 2007/0269488 | A1 | 11/2007 | Ravi |
| 2007/0282057 | A1 | 12/2007 | Mentak et al. |
| 2009/0088493 | A1 | 4/2009 | Laredo et al. |
| 2009/0088544 | A1 | 4/2009 | Laredo |
| 2009/0093604 | A1 | 4/2009 | Schlueter |
| 2011/0046258 | A1 | 2/2011 | Laredo |

FOREIGN PATENT DOCUMENTS

| | | |
|---|---|---|
| FR | 2808201 | 4/2000 |
| JP | 2005160565 | 6/2005 |
| WO | WO0118078 A1 | 3/2001 |
| WO | WO2007149083 A1 | 12/2007 |
| WO | WO2008011566 A2 | 1/2008 |

OTHER PUBLICATIONS

De Groot, Jacqueline H., Injectable Intraocular Lens Materials Based Upon Hydrogels, Biomacromolecules, 2001, pp. 628-634, vol. 2.

*Primary Examiner* — Tae H Yoon
(74) *Attorney, Agent, or Firm* — Patrick M. Ryan

(57) ABSTRACT

High refractive index copolymers with reduced glistenings are disclosed. The copolymers, which are particularly suitable for use as ophthalmic device materials, comprise a high molecular weight, reactive, linear polyethylene glycol component.

20 Claims, No Drawings

HIGH REFRACTIVE INDEX, ACRYLIC OPHTHALMIC DEVICE MATERIALS WITH REDUCED GLISTENINGS

CROSS-REFERENCE TO RELATED APPLICATIONS

This application claims priority under 35 U.S.C. §119 to U.S. Provisional Patent Application No. 61/356,963, filed Jun. 21, 2010, the entire contents of which are incorporated herein by reference.

FIELD OF THE INVENTION

This invention is directed to ophthalmic and otorhinolaryngological device materials. In particular, this invention relates to soft, high refractive index acrylic device materials that have improved glistening resistance.

BACKGROUND OF THE INVENTION

With advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Conventional silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a high refractive index and unfold more slowly or controllably than conventional silicone materials.

U.S. Pat. No. 5,290,892 discloses high refractive index, acrylic materials suitable for use as an intraocular lens ("IOL") material. These acrylic materials contain, as principal components, two aryl acrylic monomers. The IOLs made of these acrylic materials can be rolled or folded for insertion through small incisions.

U.S. Pat. No. 5,331,073 also discloses soft acrylic IOL materials. These materials contain as principal components, two acrylic monomers which are defined by the properties of their respective homopolymers. The first monomer is defined as one in which its homopolymer has a refractive index of at least about 1.50. The second monomer is defined as one in which its homopolymer has a glass transition temperature less than about 22° C. These IOL materials also contain a cross-linking component. Additionally, these materials may optionally contain a fourth constituent, different from the first three constituents, which is derived from a hydrophilic monomer. These materials preferably have a total of less than about 15% by weight of a hydrophilic component.

U.S. Pat. No. 5,693,095 discloses foldable, high refractive index ophthalmic lens materials containing at least about 90 wt. % of only two principal components: one aryl acrylic hydrophobic monomer and one hydrophilic monomer. The aryl acrylic hydrophobic monomer has the formula

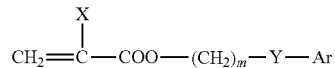

wherein: X is H or $CH_3$;

m is 0-6;

Y is nothing, O, S, or NR, wherein R is H, $CH_3$, $C_nH_{2n+1}$ (n=1-10), iso-$OC_3H_7$, $C_6H_5$, or $CH_2C_6H_5$; and Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$.

The lens materials described in the '095 patent preferably have a glass-transition temperature ("$T_g$") between about −20 and +25° C.

Flexible intraocular lenses may be folded and inserted through a small incision. In general, a softer material may be deformed to a greater extent so that it can be inserted through an increasingly smaller incision. Soft acrylic or methacrylic materials typically do not have an appropriate combination of strength, flexibility and non-tacky surface properties to permit IOLs to be inserted through an incision as small as that required for silicone IOLs.

Polyethylene glycol (PEG) dimethacrylates are known to improve glistening resistance of hydrophobic acrylic formulations. See, for example, U.S. Pat. Nos. 5,693,095 and 6,353,069. Both the concentration and molecular weight of PEG dimethacrylates have an impact on glistening performance. Generally, use of higher molecular weight PEG dimethacrylates (1000 MW) yield copolymers with improved glistening performance at low PEG concentrations (10-15 wt %), as compared to lower molecular weight PEG dimethacrylates (<1000 MW). However, low PEG dimethacrylate concentrations are desirable to maintain a high refractive index copolymer. Addition of PEG dimethacrylates also tends to decrease the modulus and tensile strength of the resulting copolymer.

SUMMARY OF THE INVENTION

Improved soft, foldable acrylic device materials which are particularly suited for use as IOLs, but which are also useful as other ophthalmic or otorhinolaryngological devices, such as contact lenses, keratoprostheses, corneal rings or inlays, otological ventilation tubes and nasal implants, have been discovered. These polymeric materials comprise a high molecular weight, reactive, linear polyethylene glycol component.

Among other factors, the present invention is based on the finding that use of high molecular weight, reactive, linear polyethylene glycol components in acrylic intraocular lens formulations efficiently reduces or eliminates temperature-induced glistening formation in hydrophobic acrylic copolymers. The subject monomers allow synthesis of glistening resistant, low equilibrium water content, high refractive index IOLs.

DETAILED DESCRIPTION OF THE INVENTION

Unless indicated otherwise, all component amounts are presented on a % (w/w) basis ("wt. %").

The ophthalmic device materials are formed by copolymerizing a composition comprising
a) 50-93% of a polymerizable monomer of the structure:

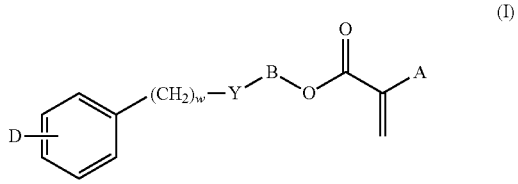

wherein: A is H or $CH_3$;
B is $(CH_2)_m$ or $[O(CH_2)_2]_z$;
m is 2-6;
z is 1-10;
Y is nothing, O, S, or NR', provided that if Y is O, S, or NR', then B is $(CH_2)_m$;
R' is H, $CH_3$, $C_nH_{2n'+1}$, iso-$OC_3H_7$, $C_6H_5$, or $CH_2C_6H_5$;
n'=1-10;
w is 0-6, provided that m+w≦8; and
D is H, Cl, Br, $C_1$-$C_4$ alkyl, $C_1$-$C_4$ alkoxy, $C_6H_5$, or $CH_2C_6H_5$;
b) 1-5% of a high molecular weight, linear polyethylene glycol component of the structure:

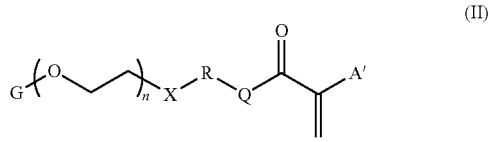

wherein: X, X' independently=nothing, O, or NH;
R, R' independently=nothing or $(CH_2)_p$;
p=1-3;
Q, Q' independently=nothing or $C(=O)NHCH_2CH_2O$;
A'=H or $CH_3$;
G=H, $C_1$-$C_4$ alkyl, $(CH_2)_mNH_2$, $(CH_2)_mCO_2H$, or R'—X'—Q'—$C(=O)C(=CH_2)$A'; and
n=45-225 when G=H, $C_1$-$C_4$ alkyl, $(CH_2)_mNH_2$, or $(CH_2)_mCO_2H$; otherwise, n=51-225; and
c) a polymerizable cross-linking agent.

These device materials can be used to form intraocular lenses with low surface tack and high refractive indexes. Lenses made of these materials are flexible and transparent, can be inserted into the eye through a relatively small incision, and recover their original shape after having been inserted.

Monomers of structure (I) can be made by methods known in the art. For example, the conjugate alcohol of the desired monomer can be combined in a reaction vessel with methyl acrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding acrylic acid to the conjugate alcohol and catalyzing with a carbodiimide or mixing the conjugate alcohol with acryloyl chloride and a base such as pyridine or triethylamine.

Suitable monomers of structure (I) include, but are not limited to: 2-ethylphenoxy acrylate; phenyl acrylate; benzyl acrylate; 2-phenylethyl acrylate; 3-phenylpropyl acrylate; 4-phenylbutyl acrylate; 4-methylphenyl acrylate; 4-methylbenzyl acrylate; 2-2-methylphenylethyl acrylate; 2-3-methylphenylethyl acrylate; 2-4-methylphenylethyl acrylate; 2-(4-propylphenyl)ethyl acrylate; 2-(4-(1-methylethyl)phenyl)ethyl acrylate; 2-(4-methoxyphenyl)ethyl acrylate; 2-(4-cyclohexylphenyl)ethyl acrylate; 2-(2-chlorophenyl)ethyl acrylate; 2-(3-chlorophenyl)ethyl acrylate; 2-(4-chlorophenyl)ethyl acrylate; 2-(4-bromophenyl)ethyl acrylate; 2-(3-phenylphenyl)ethyl acrylate; 2-(4-phenylphenyl)ethyl acrylate; 2-(4-benzylphenyl)ethyl acrylate; and their corresponding methacrylates.

Preferred monomers of formula (I) are those wherein B is $(CH_2)_m$, m is 2-5, Y is nothing or O, w is 0-1, and D is H. Most preferred are 2-phenylethyl acrylate; 4-phenylbutyl acrylate; 5-phenylpentyl acrylate; 2-benzyloxyethyl acrylate; 3-benzyloxypropyl acrylate; and their corresponding methacrylates.

Although the total amount of the monomer of structure (I) contained in the device materials of the present invention is generally 50-94% by weight, and is preferably 50-80% by weight, of the total amount of polymerizable components of the ophthalmic device materials, such amount may comprise one monomer of structure (I) or combinations of monomers of structure (I).

In addition to the monomer(s) of structure (I), the copolymeric device materials of the present invention comprise 1-5% of a high molecular weight, linear polyethylene glycol component of structure (II). The polyethylene glycol component of the high molecular weight, linear polyethylene glycol component of structure (II) has a number average molecular weight of 2,000-10,000 Daltons, preferably 2,000-8,000 Daltons, more preferably 2,000-6,000 Daltons, and most preferably 2,500-6,000 Daltons.

Macromers of structure (II) can be made by methods known in the art. Generally, a hydroxyl terminated polyethylene glycol, mono- or di-terminated, is dissolved in tetrahydrofuran and treated with a (meth)acrylic acid derivative such as methacryloyl chloride or methacrylic anhydride in the presence of triethylamine or pyridine. The reaction proceeds until greater than 90% of the hydroxyl groups have been converted to the corresponding methacrylic esters. The polymer solution is filtered and the polymer is isolated by precipitation into diethyl ether. Amine and carboxylic acid terminated polyethylene glycols are functionalized in a similar manner using suitable (meth)acrylic acid derivatives. For example, the following macromers may be synthesized:

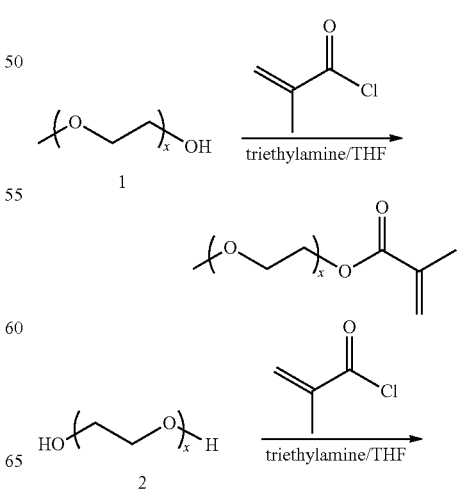

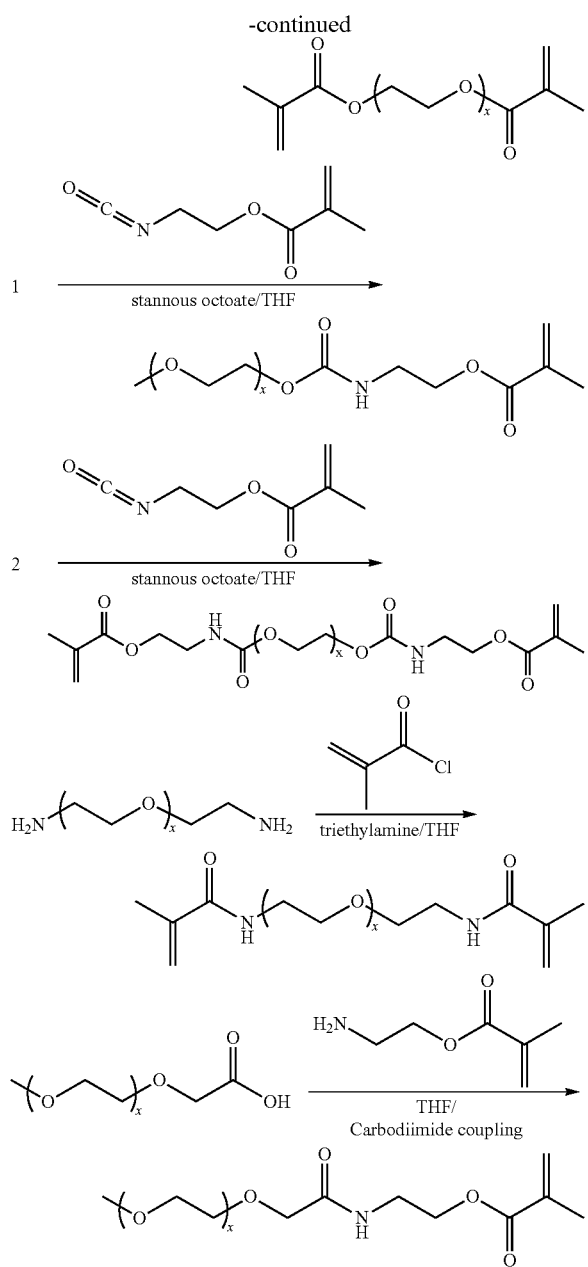

Preferred monomers of structure (II) are those wherein:
X, X' independently=nothing or O;
R, R'=nothing;
Q, Q' independently=nothing or C(=O)NHCH$_2$CH$_2$O;
A'=H or CH$_3$;
G=C$_1$-C$_4$ alkyl or R'—X'-Q'—C(=O)C(=CH$_2$)A'; and
n=45-180 when G=C$_1$-C$_4$ alkyl; otherwise, n=51-225.

Although the total amount of the monomer of structure (II) contained in the device materials of the present invention is 1-5% by weight, is preferably 2-5% by weight, and is most preferably 2-4% by weight, of the total amount of polymerizable components of the device materials, such amount may comprise one monomer of structure (II) or combinations of monomers of structure (II).

The ophthalmic device materials of the present invention also contain a polymerizable cross-linking agent. The cross-linking agent may be any terminally ethylenically unsaturated compound having more than one unsaturated group. Suitable cross-linking agents include, for example: ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; CH$_2$=C(CH$_3$)C(=O)O—(CH$_2$CH$_2$O)$_p$—C(=O)C(CH$_3$)=CH$_2$ where p=1-50; and CH$_2$=C(CH$_3$)C(=O)C(CH$_2$)$_t$O—C(=O)C(CH$_3$)=CH$_2$ where t=3-20; and their corresponding acrylates. A preferred cross-linking monomer is CH$_2$=C(CH$_3$)C(=O)O—(CH$_2$CH$_2$O)$_p$—C(=O)C(CH$_3$)=CH$_2$ where p is such that the number-average molecular weight is about 400, about 600, or about 1000. Other preferred cross-linking monomers are ethylene glycol dimethacrylate (EGDMA), diethylene glycol dimethacrylate, triethylene glycol dimethacrylate, triethylene glycol diacrylate, and 1,4-butanediol diacrylate (BDDA).

Generally, the total amount of the cross-linking component is at least 0.1% by weight and, depending on the identity and concentration of the remaining components and the desired physical properties, can range to about 20% by weight. The preferred concentration range for the cross-linking component is 1-5% for small, hydrophobic compounds with molecular weights typically less than 500 Daltons, and 5-17% (w/w) for larger, hydrophilic compounds.

In addition to one or more monomers of structure (I), one or more monomers of structure (II), and one or more cross-linking agents, the copolymeric device materials of the present invention may also contain other ingredients, including, but not limited to, UV-absorbers, colored dyes, additives to reduce tack, and siloxane monomers of structure (III).

An ultra-violet absorbing agent can also be included in the materials of the present invention. The ultraviolet absorbing agent can be any compound which absorbs ultraviolet light, i.e., light having a wavelength shorter than about 400 nm, but does not absorb any substantial amount of visible light. The ultraviolet absorbing compound is incorporated into the monomer mixture and is entrapped in the polymer matrix when the monomer mixture is polymerized. Suitable ultraviolet absorbing compounds include substituted benzophenones, such as 2-hydroxybenzophenone, and 2-(2-hydroxyphenyl)benzotriazoles. It is preferred to use an ultraviolet absorbing compound which is copolymerizable with the monomers and is thereby covalently bound to the polymer matrix. In this way possible leaching of the ultraviolet absorbing compound out of the lens and into the interior of the eye is minimized. Examples of suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. A preferred ultraviolet absorbing compound is 2-(2'-hydroxy-3'-methallyl-5'-methyl phenyl) benzotriazole.

In addition to ultraviolet absorbing materials, ophthalmic devices made of the copolymers of the present invention may include colored dyes, such as the yellow dyes disclosed in U.S. Pat. No. 5,470,932.

The device materials of the present invention may also contain additives to reduce or eliminate tack. Examples of such additives include those disclosed in U.S. Pat. Nos. 7,585,900 and 7,714,039, the entire contents of which are incorporated by reference herein.

In one embodiment, the device materials of the present invention also contain a siloxane monomer of structure (III)

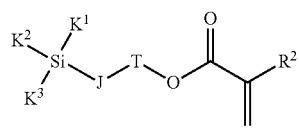
(III)

wherein
$R^2$ is H or $CH_3$;
T is nothing, $O(CH_2)_b$, or $OCH_2CH(OH)CH_2$;
b is 1-3;
J is $(CH_2)_z$; and
$K^1$, $K^2$, and $K^3$ independently are $CH_3$, $C_6H_5$, or $OSi(CH_3)_3$.

Monomers of structure (III) may be made by known methods and in some cases are commercially available. Preferred monomers of structure (III) are those wherein $R^2$ is $CH_3$, T is nothing or $OCH_2CH(OH)CH_2$, J is $(CH_2)_3$, and $K^1$, $K^2$, and $K^3$ independently are $CH_3$, $C_6H_5$, or $OSi(CH_3)_3$.

Most preferred monomers of structure (III) are those selected from the group consisting of:
3-[tris(trimethylsilyloxy)silyl]-propyl methacrylate ("TRIS");
3-(methacryloxy-2-hydroxypropoxy)propylmethylbis(trimethoxy)silane (SiMA);
methacryloxypropylpentamethyldisiloxane;
3-methacryloxypropylbis(trimethylsiloxy)methylsilane;
methacryloxymethyltris(trimethylsiloxy)silane;
(methacryloxymethyl)phenyl-dimethylsilane; and
(methacryloxymethyl)bis(trimethylsiloxy)methylsilane.

The amount of monomer of structure (III) in the materials of the present invention will range from 5-30%, preferably 5-25%, and most preferably 5-15%.

The proportions of the monomers to be included in the copolymeric device materials of the present invention should be chosen so that the resulting copolymer has a glass transition temperature ($T_g$) not greater than about 37° C., which is normal human body temperature. Copolymers having glass transition temperatures higher than 37° C. are not suitable for use in foldable IOLs; such lenses could only be rolled or folded at temperatures above 37° C. and would not unroll or unfold at normal body temperature. It is preferred to use copolymers having a glass transition temperature somewhat below normal body temperature and no greater than normal room temperature, e.g., about 20-25° C., in order that IOLs made of such copolymers can be rolled or folded conveniently at room temperature. $T_g$ is measured by differential scanning calorimetry at 10° C./min., and is determined at the midpoint of the transition of the heat flux curve.

For use in IOLs, the materials of the present invention preferably exhibit sufficient strength to allow devices made of them to be folded or manipulated without fracturing. Thus, the copolymers of the present invention will have an elongation (% strain at break) of at least 100%, preferably at least 130%, and most preferably between 130 and 300%. This property indicates that lenses made of such materials generally will not crack, tear or split when folded. Elongation of polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at ambient conditions using an Instron Material Tester (Model No. 4442 or equivalent) with a 50 Newton load cell. The grip distance is set at 14 mm and a crosshead speed is set at 500 mm/minute and the sample is pulled until failure. The elongation (strain) is reported as a fraction of the displacement at failure to the original grip distance. Since the materials to be tested are essentially soft elastomers, loading them into the Instron machine tends to make them buckle. To remove the slack in the material sample a pre-load is placed upon the sample. This helps to reduce the slack and provide a more consistent reading. Once the sample is pre-loaded to a desired value (typically 0.03 to 0.05 N) the strain is set to zero and the test is begun.

The device materials of the present invention preferably have a refractive index of 1.53 to 1.56 in their fully hydrated state at 35° C. For IOL applications, the stiffness of the device material must be low enough to permit folding and injection through a small diameter opening (e.g., 1-3 mm) without tearing or deforming after injection. In a preferred embodiment, the Young's Modulus of the device material will be less than 60 MPa, preferably less than 50 MPa, and most preferably between 5-40 MPa.

The copolymeric device materials preferably have an equilibrium water content of less than 2.0 weight % across the temperature range of 16-45° C. and preferably less than 2.5 weight % in the temperature range of 16-23° C. The device materials are preferably resistant to glistenings such that when equilibrated in water at 45° C. and subsequently allowed to cool to ambient temperature (approximately 22° C.) should produce very few to no microvacuoles as detected by microscopic examination.

The copolymers of this invention are prepared by conventional polymerization methods. For example, a mixture of the liquid monomers of structure (I), structure (II), and a cross-linking agent in the desired proportions, together with any other polymerizable components, such as a UV absorber, yellow dye, and/or additive to reduce tack, and a conventional thermal free-radical initiator is prepared. The mixture can then be introduced into a mold of desired shape, and the polymerization carried out by heating to activate the initiator. Typical thermal free radical initiators include peroxides, such as benzoyl peroxide, peroxycarbonates, such as bis-(4-t-butylcyclohexyl) peroxydicarbonate, azonitriles, such as azobisisobutyronitrile (AIBN), and the like. A preferred initiator is AIBN. Alternatively, the monomers can be photopolymerized by using a mold which is transparent to actinic radiation of a wavelength capable of initiating polymerization. Conventional photoinitiator compounds, e.g., a benzophenone-type or bisacylphosphine oxide (BAPO) photoinitiator, can also be introduced to facilitate the polymerization. Regardless of the chosen initiator or curing method, the curing process should be controlled to avoid rapid polymerization, which may yield polymerized materials having more tack than the same materials polymerized more slowly.

Once the ophthalmic device materials of the present invention have been cured, they are extracted in a suitable solvent to remove as much of the unreacted components of the materials as possible. Examples of suitable solvents include acetone, methanol, and cyclohexane. A preferred solvent for extraction is acetone.

IOLs constructed of the disclosed ophthalmic device materials can be of any design capable of being rolled or folded into a small cross section that can fit through a relatively smaller incision. For example, the IOLs can be of what is known as a one piece or multipiece design. Typically, an IOL comprises an optic and at least one haptic. The optic is that portion which serves as the lens and the haptics are like arms which hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the ophthalmic device materials of the present invention are also suitable for use in other devices, including contact lenses, keratoprostheses, intracorneal lenses, corneal inlays or rings, and glaucoma filtration devices.

The invention will be further illustrated by the following examples which are intended to be illustrative, but not limiting.

Example 1

A representative IOL formulation is shown in Table 1. It may be prepared as follows. Components are taken from the refrigerator, freezer or cabinet and set on lab bench for about 2 hours. The components are weighed in the indicated ratios, dissolved, and vortex mixed in a 40 ml glass vial. The formulation is purged with nitrogen for 2 minutes, placed under high vacuum (<0.5 mm Hg) for 2 minutes, injected through a 0.2 micron PTFE filter into standard polypropylene slab molds or lens wafers, and then heated: room temp. to 70° C. (20 min. ramp), 70° C. (60 min. soak), 70-110° C. (20 min. ramp), 110° C. (120 min. soak).

TABLE 1

| Component | % (w/w) |
| --- | --- |
| phenylethyl acrylate (PEA) | 73.6 |
| phenylethyl methacrylate (PEMA) | 20.1 |
| 1,4-butanediol diacrylate (BDDA) | 1.5 |
| 3-(3-tert-butyl-4-hydroxy-5-(5-methoxy-2H-benzo[d]-[1,2,3]-triazol-2-yl)phenoxy)propyl methacrylate | 1.8 |
| 2-hydroxy-3-((4-methoxyphenyl)-diazenyl)-5-methylbenzyl methacrylate | 0.02 |
| IEMA functionalized PEG5000 monomethyl ether | 3.0 |
| 2,2'-Azobis(2-methylpropionitrile) | 0.5 |

Example 2

Synthesis of 5,000 MW PEG-Methacrylate

In a 250 ml round bottom flask equipped with magnetic stirrer was dissolved 24 g (5.0 mmol) poly(ethylene glycol) monomethyl ether (Mn=5,000, Aldrich, Milwaukee, Wis.), 1.5 g (9.6 mmol) 2-isocyanatoethyl methacrylate (IEMA) (Aldrich), and 50 mg (0.1 mmol) stannous octoate in 100 ml THF (Aldrich, inhibited with MEHQ). The reaction mixture was heated to 60° C. for 20 hours. The reaction mixture was poured dropwise into diethyl ether to precipitate the polymer. The polymer was filtered using a fritted funnel with medium pore size. The polymer was redissolved in THF and precipitated a total of 3 times and then dried at ambient temperature and high vacuum (0.1 mm Hg) to give 21 g (86%) of a white solid with Mn=8,600, Mw=9,000, Mz=9,400, PDI=1.04 using polystyrene standards. Purity was estimated at greater than 98% by GPC.

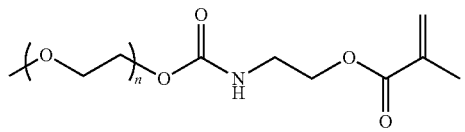

Example 3

Crosslinked Polymers

The high molecular weight, linear polyethylene glycol component of Example 2 was formulated as shown in Table 2. Test samples measuring 0.9 mm in thickness were thermally cured at 70° C. for 1 hour and 110° C. for 2 hours. Samples were extracted in acetone for 5 hours at 55° C. or 20 hours at ambient temperature and then dried slowly at ambient temperature for 20 hours, followed by vacuum (0.1 mm Hg) for a minimum of 20 hours at 70° C.

Weight percent extractables, equilibrium water content (EWC), and slab appearance of hydrated samples that were subjected to a 45-22° C. delta T test are shown in Table 3.

Linear polyethylene glycol diacrylate having a number average molecular weight of 4,000 Daltons was also formulated as shown in Table 4 and Table 6. A formulation comprised of 82.5% PEA, 2.00% polyethylene glycol dimethacrylate (average $M_n$=6,000 Da), 14.0% HEMA, and 1.52% TEGDMA appeared homogeneous, but could not be filtered through 0.2 or 1.0 micron PTFE filters so test samples were not prepared.

TABLE 2

| | Example (% w/w) | | | |
| --- | --- | --- | --- | --- |
| Component | 3A | 3B | 3C | 3D |
| Ex 2 | 2.99 | 0 | 0 | 3.06 |
| polyPEGMA | 0 | 3.02 | 0 | 0 |
| PEA | 73.6 | 73.6 | 75.9 | 72.9 |
| PEMA | 20.1 | 20.1 | 20.7 | 20.0 |
| BDDA | 1.50 | 1.50 | 1.54 | 1.51 |
| UV-13 | 1.80 | 1.80 | 1.85 | 0 |
| WL-1 | 0 | 0 | 0 | 1.50 |
| 2-hydroxy-3-((4-methoxyphenyl)-diazenyl)-5-methylbenzyl methacrylate | 0.0194 | 0.0194 | 0.020 | 0.020 |
| PSMA | 0 | 0 | 0 | 1.00 |
| Perkadox 16s | 0 | 0 | 0 | 1.00 |
| AIBN | 0.52 | 0.56 | 0.62 | 0 |

PEA = phenylethyl acrylate
PEMA = phenylethyl methacrylate
BDDA = 1,4-butanediol diacrylate
polyPEGMA = methacrylate terminated polymer with $M_n$ = 4,100 derived from PEG(550) monomethyl ether methacrylate
UV-13 = 3-(3-tert-butyl-4-hydroxy-5-(5-methoxy-2H-benzo[d][1,2,3]-triazol-2-yl)phenoxy)propyl methacrylate
WL-1 = 2-hydroxy-5-methoxy-3-(5-(trifluoro-methyl)-2H-benzo[d][1,2,3]-triazol-2-yl)benzyl methacrylate
PSMA = methacrylate terminated polystyrene, avg. $M_n$ = 12,000
AIBN = 2,2'-azobisisobutyronitrile or 2,2'-Azobis(2-methylpropionitrile)

TABLE 3

| Example | % Extractables (N = 8) | EWC (35° C.) (wt. %) | Sample Appearance After Delta T Test | Glistenings Per Test Sample |
| --- | --- | --- | --- | --- |
| 3A | 2.0 | 1.2 | [1]Clear | 0 |
| 3B | 2.3 | 1.1 | [1]Clear | 0 |

TABLE 3-continued

| Example | % Extractables (N = 8) | EWC (35° C.) (wt. %) | Sample Appearance After Delta T Test | Glistenings Per Test Sample |
|---|---|---|---|---|
| 3C | 2.1 | 0.6 | [1]Clear | many |
| 3D | 1.4 | 1.2 | [1]Clear | 0 |

[1]Samples were equilibrated in deionized water for 1 day at 45° C., then cooled to ambient temperature and inspected by an optical microscope 1-2 hours later using 100X magnification under bright field conditions

TABLE 4

| | Example (% w/w) | | |
|---|---|---|---|
| Component | 3E | 3F | 3G |
| PEG4000-DA | 1.50 | 2.01 | 2.50 |
| PEA | 81.2 | 80.7 | 80.2 |
| HEMA | 14.0 | 14.0 | 14.0 |
| TEGDMA | 1.50 | 1.51 | 1.50 |
| oMTP | 1.80 | 1.80 | 1.80 |
| tBPO | 1.0 | 1.0 | 1.0 |

PEG4000-DA = poly(ethylene glycol) diacrylate, average $M_n \sim 4000$ Da
HEMA = 2-hydroxyethyl methacrylate
TEGDMA = triethylene glycol dimethacrylate
oMTP = 2-(2H-benzo[d][1,2,3]triazol-2-yl)-4-methyl-6-(2-methylallyl)phenol
WL-2 = 3-(5-fluoro-2H-benzo[d][1,2,3]triazol-2-yl)-2-hydroxy-5-methoxybenzyl methacrylate
tBPO = tert-Butyl peroxy-2-ethylhexanoate

TABLE 5

| Example | % Extractables (N = 8) | Sample Appearance After Delta T Test | Glistenings Per Test Sample |
|---|---|---|---|
| 3E | — | [1]Clear | 0 |
| 3F | 4.0 | [1]Clear | 0 |
| 3G | — | [1]Clear | 0 |

[1]Samples were equilibrated in deionized water for 1 day at 45° C., then cooled to ambient temperature and inspected by an optical microscope 1-2 hours later using 100X magnification under bright field conditions

TABLE 6

| | Example (% w/w) | | | | |
|---|---|---|---|---|---|
| Component | 3H | 3I | 3J | 3K | 3L |
| PEG4000-DA | 2.00 | 2.01 | 1.49 | 2.01 | 2.50 |
| PEA | 80.7 | 79.2 | 83.0 | 82.5 | 81.9 |
| HEMA | 14.0 | 14.0 | 14.0 | 14.0 | 14.1 |
| DEGDMA | 1.50 | 3.00 | 0 | 0 | 0 |
| TEGDMA | 0 | 0 | 1.57 | 1.54 | 1.51 |
| oMTP | 1.80 | 1.80 | 0 | 0 | 0 |
| WL-2 | 0 | 0 | 0 | 0 | 0 |
| tBPO | 1.0 | 0.99 | 0 | 0 | 0 |
| AIBN | 0 | 0 | 1.0 | 1.0 | 1.0 |

DEGDMA = Diethylene glycol dimethacrylate
WL-2 = 3-(5-fluoro-2H-benzo[d][1,2,3]triazol-2-yl)-2-hydroxy-5-methoxybenzyl methacrylate

Example 4

Tack Study

IOL materials from Example 3A-3C were tested for tack using a modified tensilometry test method. Formulation 3A contained 3% PEG-methacrylate from Example 2. Formulation 3B contained 3% of a poly[polyethylene glycol monomethyl ether methacrylate] (polyPEGMA). Formulation 3C contained no hydrophilic polymers and was used as a control. The materials were tested for tack prior to solvent extraction as shown in Table 7 and after solvent extraction as shown in Table 8. Unextracted IOL materials from Example 3E-3L were also tested for tack and results are shown in Table 9. The qualitative tack of these materials using stainless steel tweezers or forceps was deemed acceptable.

Tack Testing Procedure

Tack testing was conducted on an Instron mechanical tester using a custom fixture for measuring the metal-polymer tack or adhesion. The fixture includes a highly polished stainless steel circular stationary pin of 8 mm in diameter that is affixed to the stationary portion of the load frame. The upper (moveable) section of the load frame crosshead is attached to a circular metal platform with a hole in the center. The moveable crosshead is lowered until the bottom pin appears through the hole in the center of the upper fixture and the crosshead movement is stopped when the pin is slightly above the metal platform. The polymer sample is then placed on the protruding pin. A fresh 10 mm diameter disk is press cut from the polymer sample and is placed on the top of the protruding pin. A 300 gram weight is placed on top of the sample, pressing the sample to the pin with a uniform load. One minute after placing the weight on the sample, the Instron mechanical tester is started with a separation rate of 5 mm/min. Data is collected at a rate of 5 points/sec until the sample is pulled up off of the pin. The maximum force and area under the curve (work energy) is recorded.

Results

Six samples of each material were tested for tack and the results averaged. The values are given in Table 4 and Table 5 along with ±1 standard deviation. The pre-extraction results are less reliable because of plasticization effects of non-reacted starting material, which is different for each formulation. Results of post-extracted samples were statistically similar.

TABLE 7

| Example | Extracted Samples | Max Load (N) | Energy (mj) | Hydrophilic Component |
|---|---|---|---|---|
| 3A | no | 52 ± 7 | 8.1 ± 2.3 | 3% PEG-MA from Example 2 |
| 3B | no | 61 ± 6 | 6.2 ± 1.0 | 3% polyPEGMA |
| 3C | no | 55 ± 5 | 5.2 ± 0.6 | None (Control) |

TABLE 8

| Example | Extracted Samples | Max Load (N) | Energy (mj) | Hydrophilic Component |
|---|---|---|---|---|
| 3A | yes | 62 ± 10 | 6.4 ± 0.7 | 3% PEG-MA from Example 2 |
| 3B | yes | 58 ± 13 | 6.0 ± 1.0 | 3% polyPEGMA |
| 3C | yes | 56 ± 16 | 6.0 ± 1.8 | None (Control) |

TABLE 9

| Example | Extracted Samples | Max Load (N) | Hydrophilic Component |
|---|---|---|---|
| 3E | no | >52 | 1.5% PEG4000-DA |
| 3F | no | >52 | 2.0% PEG4000-DA |
| 3G | no | >52 | 2.5% PEG4000-DA |
| 3H | no | >52 | 2.0% PEG4000-DA |
| 3I | no | 49.8 | 2.01% PEG4000-DA |
| 3J | no | >52 | 1.5% PEG4000-DA |

TABLE 9-continued

| Example | Extracted Samples | Max Load (N) | Hydrophilic Component |
|---|---|---|---|
| 3K | no | >52 | 2.0% PEG4000-DA |
| 3L | no | >52 | 2.5% PEG4000-DA |

Example 5

A representative IOL formulation is shown in Table 10. It may be prepared as follows. Components are taken from the refrigerator, freezer or cabinet and set on lab bench for about 2 hours. The components are weighed in the indicated ratios, dissolved, and vortex mixed in a 40 ml glass vial. The formulation is purged with nitrogen for 2 minutes, placed under high vacuum (<0.5 mm Hg) for 2 minutes, injected through a 0.2 micron PTFE filter into standard polypropylene slab molds or lens wafers, and then heated: room temp. to 70° C. (20 min. ramp), 70° C. (60 min. soak), 70-110° C. (20 min. ramp), 110° C. (120 min. soak).

TABLE 10

| Component | % (w/w) |
|---|---|
| phenylethyl acrylate (PEA) | 63.6 |
| phenylethyl methacrylate (PEMA) | 20.1 |
| 3-[tris(trimethylsilyloxy)silyl]-propyl methacrylate (TRIS) | 10.0 |
| 1,4-butanediol diacrylate (BDDA) | 1.5 |
| 3-(3-tert-butyl-4-hydroxy-5-(5-methoxy-2H-benzo[d]-[1,2,3]-triazol-2-yl)phenoxy)propyl methacrylate | 1.8 |
| 2-hydroxy-3-((4-methoxyphenyl)-diazenyl)-5-methylbenzyl methacrylate | 0.02 |
| IEMA functionalized PEG5000 monomethyl ether | 3.0 |
| 2,2'-Azobis(2-methylpropionitrile) | 0.5 |

Example 6

A representative IOL formulation is shown in Table 11. It may be prepared as follows. Components are taken from the refrigerator, freezer or cabinet and set on lab bench for about 2 hours. The components are weighed in the indicated ratios, dissolved, and vortex mixed in a 40 ml glass vial. The formulation is purged with nitrogen for 2 minutes, placed under high vacuum (<0.5 mm Hg) for 2 minutes, injected through a 0.2 micron PTFE filter into standard polypropylene slab molds or lens wafers, and then heated: room temp. to 70° C. (20 min. ramp), 70° C. (60 min. soak), 70-110° C. (20 min. ramp), 110° C. (120 min. soak).

TABLE 11

| Component | % (w/w) |
|---|---|
| phenylethyl acrylate (PEA) | 61.6 |
| phenylethyl methacrylate (PEMA) | 20.1 |
| 3-[tris(trimethylsilyloxy)silyl]-propyl methacrylate (TRIS) | 10.0 |
| PDMS-1000-DMA[1] | 2.0 |
| 1,4-butanediol diacrylate (BDDA) | 1.5 |
| 3-(3-tert-butyl-4-hydroxy-5-(5-methoxy-2H-benzo[d]-[1,2,3]-triazol-2-yl)phenoxy)propyl methacrylate | 1.8 |
| 2-hydroxy-3-((4-methoxyphenyl)-diazenyl)-5-methylbenzyl methacrylate | 0.02 |
| IEMA functionalized PEG5000 monomethyl ether | 3.0 |
| 2,2'-Azobis(2-methylpropionitrile) | 0.5 |

[1]PDMS-1000-DMA = methacryloxypropyl terminated dimethylsiloxane polymer having a molecular weight about 1,000 Daltons and viscosity from 12-18 cst.

Example 7

A representative IOL formulation is shown in Table 12. It may be prepared as follows. Components are taken from the refrigerator, freezer or cabinet and set on lab bench for about 2 hours. The components are weighed in the indicated ratios, dissolved, and vortex mixed in a 40 ml glass vial. The formulation is purged with nitrogen for 2 minutes, placed under high vacuum (<0.5 mm Hg) for 2 minutes, injected through a 0.2 micron PTFE filter into standard polypropylene slab molds or lens wafers, and then heated: room temp. to 70° C. (20 min. ramp), 70° C. (60 min. soak), 70-110° C. (20 min. ramp), 110° C. (120 min. soak).

TABLE 12

| Component | % (w/w) |
|---|---|
| phenylethyl acrylate (PEA) | 71.6 |
| 2-hydroxyethyl methacrylate (HEMA) | 10.0 |
| 3-[tris(trimethylsilyloxy)silyl]-propyl methacrylate (TRIS) | 10.0 |
| PDMS-1000-DMA[1] | 2.0 |
| 1,4-butanediol diacrylate (BDDA) | 1.5 |
| 3-(3-tert-butyl-4-hydroxy-5-(5-methoxy-2H-benzo[d]-[1,2,3]-triazol-2-yl)phenoxy)propyl methacrylate | 1.8 |
| 2-hydroxy-3-((4-methoxyphenyl)-diazenyl)-5-methylbenzyl methacrylate | 0.02 |
| IEMA functionalized PEG5000 monomethyl ether | 3.0 |
| 2,2'-Azobis(2-methylpropionitrile) | 0.5 |

[1]PDMS-1000-DMA = methacryloxypropyl terminated dimethylsiloxane polymer having a molecular weight about 1,000 Daltons and viscosity from 12-18 cst.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. A polymeric ophthalmic or otorhinolaryngological device material comprising a) 50-93% of a polymerizable monomer of the structure:

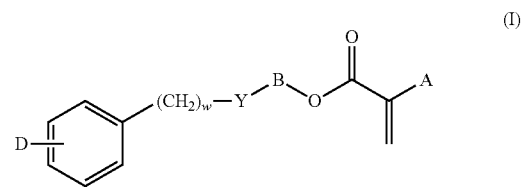

(I)

wherein: A is H or $CH_3$;

B is $(CH_2)_m$ or $[O(CH_2)_2]_z$;

m is 2-6;

z is 1-10;

Y is nothing, O, S, or NR', provided that if Y is O, S, or NR', then B is $(CH_2)_m$;

R' is H, $CH_3$, $C_nH_{2n'+1}$, iso-$OC_3H_7$, $C_6H_5$, or $CH_2C_6H_5$;

n'=1-10;

w is 0-6, provided that m+w≦8; and

D is H, Cl, Br, $C_1$-$C_4$ alkyl, $C_1$-$C_4$ alkoxy, $C_6H_5$, or $CH_2C_6H_5$;

b) 1-5% of a high molecular weight, linear polyethylene glycol component of the structure:

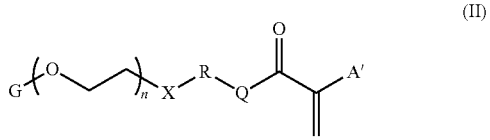

wherein: X, X' independently=nothing, O, or NH;
R, R' independently=nothing or $(CH_2)_p$;
p=1-3;
Q, Q' independently=nothing or $C(=O)NHCH_2CH_2O$;
A'=H or $CH_3$;
G=H, $C_1$-$C_4$ alkyl, $(CH_2)_mNH_2$, $(CH_2)_mCO_2H$, or R'—X'—Q'—C(=O)C(=CH_2)A'; and
n=45-225 when G=H, $C_1$-$C_4$ alkyl, $(CH_2)_mNH_2$, or $(CH_2)_mCO_2H$; otherwise, n=51-225; and
c) a polymerizable cross-linking agent.

2. The polymeric device material of claim 1 wherein the monomer of structure (I) is selected from the group consisting of: 2-ethylphenoxy acrylate; phenyl acrylate; benzyl acrylate; 2-phenylethyl acrylate; 3-phenylpropyl acrylate; 4-phenylbutyl acrylate; 4-methylphenyl acrylate; 4-methylbenzyl acrylate; 2-2-methylphenylethyl acrylate; 2-3-methylphenylethyl acrylate; 2-4-methylphenylethyl acrylate; 2-(4-propylphenyl)ethyl acrylate; 2-(4-(1-methylethyl)phenyl)ethyl acrylate; 2-(4-methoxyphenyl)ethyl acrylate; 2-(4-cyclohexylphenyl)ethyl acrylate; 2-(2-chlorophenyl)ethyl acrylate; 2-(3-chlorophenyl)ethyl acrylate; 2-(4-chlorophenyl)ethyl acrylate; 2-(4-bromophenyl)ethyl acrylate; 2-(3-phenylphenyl)ethyl acrylate; 2-(4-phenylphenyl)ethyl acrylate; 2-(4-benzylphenyl)ethyl acrylate; 2-ethylphenoxy methacrylate; phenyl methacrylate; benzyl methacrylate; 2-phenylethyl methacrylate; 3-phenylpropyl methacrylate; 4-phenylbutyl methacrylate; 4-methylphenyl methacrylate; 4-methylbenzyl methacrylate; 2-2-methylphenylethyl methacrylate; 2-3-methylphenylethyl methacrylate; 2-4-methylphenylethyl methacrylate; 2-(4-propylphenyl)ethyl methacrylate; 2-(4-(1-methylethyl)phenyl)ethyl methacrylate; 2-(4-methoxyphenyl)ethyl methacrylate; 2-(4-cyclohexylphenyl)ethyl methacrylate; 2-(2-chlorophenyl)ethyl methacrylate; 2-(3-chlorophenyl)ethyl methacrylate; 2-(4-chlorophenyl)ethyl methacrylate; 2-(4-bromophenyl)ethyl methacrylate; 2-(3-phenylphenyl)ethyl methacrylate; 2-(4-phenylphenyl)ethyl methacrylate; and 2-(4-benzylphenyl)ethyl methacrylate.

3. The polymeric device material of claim 1 wherein for the monomer of structure (I): B is $(CH_2)_m$, m is 2-5, Y is nothing or O, w is 0-1, and D is H.

4. The polymeric device material of claim 3 wherein the monomer of structure (I) is selected from the group consisting of: 2-phenylethyl acrylate; 4-phenylbutyl acrylate; 5-phenylpentyl acrylate; 2-benzyloxyethyl acrylate; 3-benzyloxypropyl acrylate; 2-phenylethyl methacrylate; 4-phenylbutyl methacrylate; 5-phenylperityl methacrylate; 2-benzyloxyethyl methacrylate; and 3-benzyloxypropyl methacrylate.

5. The polymeric device material of claim 1 wherein the amount of monomer of structure (I) is 75-90% (w/w).

6. The polymeric device material of claim 1 wherein for the monomer of structure (II):
X, X' independently=nothing or O;
R, R'=nothing;
Q, Q' independently=nothing or $C(=O)NHCH_2CH_2O$;
A'=H or $CH_3$;
G=$C_1$-$C_4$ alkyl or R'—X'-Q'—C(=O)C(=CH_2)A'; and
n=45-180 when G=$C_1$-$C_4$ alkyl; otherwise, n=51-225.

7. The polymeric device material of claim 1 wherein for the monomer of structure (II) has a polyethylene glycol component having a number average molecular weight of 2,000-8,000 Daltons.

8. The polymeric device material of claim 7 wherein the monomer of structure (II) has a polyethylene glycol component having a number average molecular weight of 2,000-6,000 Daltons.

9. The polymeric device material of claim 8 wherein the monomer of structure (II) has a polyethylene glycol component having a number average molecular weight of 2,500-6,000 Daltons.

10. The polymer device material of claim 1 wherein the amount of monomer of structure (II) is 2-5% (w/w).

11. The polymeric device material of claim 10 wherein the amount of monomer of structure (II) is 2-4% (w/w).

12. The polymeric device material of claim 1 wherein the cross-linking monomer is selected from the group consisting of: ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; $CH_2=C(CH_3)C(=O)O-(CH_2CH_2O)_p-C(=O)C(CH_3)=CH_2$ where p=1-50; and $CH_2=C(CH_3)C(=O)O(CH_2)_tO-C(=O)C(CH_3)=CH_2$ where t=3-20; and their corresponding acrylates.

13. The polymeric device material of claim 12 wherein the cross-linking monomer is selected from the group consisting of ethylene glycol dimethacrylate; diethylene glycol dimethacrylate; triethylene glycol dimethacrylate; triethylene glycol diacrylate; 1,4-butanediol diacrylate; and $CH_2=C(CH_3)C(=O)O-(CH_2CH_2O)_p-C(=O)C(CH_3)=CH_2$ where p is such that the number-average molecular weight is about 400, about 600, or about 1000.

14. The polymeric device material of claim 1 further comprising an ingredient selected from the group consisting of polymerizable UV absorbers and polymerizable colorants.

15. The polymeric device material of claim 14 comprising 0.1-5% (w/w) of a polymerizable UV absorber and 0.01-0.5% (w/w) of a polymerizable colorant.

16. The polymeric device material of claim 1 wherein the polymeric device material has an equilibrium water content of less than 2.0 weight % across the temperature range of 16-45° C.

17. The polymeric device material of claim 1 wherein the polymeric device material further comprises a siloxane monomer of the structure:

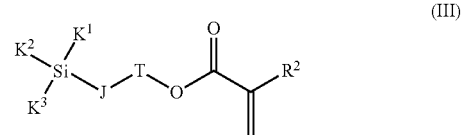

wherein
$R^2$ is H or $CH_3$;
T is nothing, $O(CH_2)_b$, or $OCH_2CH(OH)CH_2$;
b is 1-3;
J is $(CH_2)_z$; and
$K^1$, $K^2$, and $K^3$ independently are $CH_3$, $C_6H_5$, or $OSi(CH_3)_3$.

18. The polymeric device material of claim 1 wherein the polymeric device material further comprises 2-hydroxyethyl methacrylate.

19. An ophthalmic or otorhinolaryngological device comprising the polymeric device material of claim 1 wherein the ophthalmic or otorhinolaryngological device is selected from the group consisting of intraocular lenses; contact lenses; keratoprostheses; corneal inlays or rings; otological ventilation tubes; and nasal implants.

20. The ophthalmic or otorhinolaryngological device of claim 17 wherein the ophthalmic or otorhinolaryngological device is an intraocular lens.

\* \* \* \* \*